United States Patent
Perkins et al.

(10) Patent No.: US 6,666,894 B2
(45) Date of Patent: Dec. 23, 2003

(54) ATTACHMENT SYSTEM FOR PROSTHESIS

(76) Inventors: Dale Perkins, 542 Addison Ave. W., Twin Falls, ID (US) 83301; Matt Perkins, 542 Addison Ave. W., Twin Falls, ID (US) 83301

(*) Notice: Subject to any disclaimer, the term of this patent is extended or adjusted under 35 U.S.C. 154(b) by 0 days.

(21) Appl. No.: 09/972,729

(22) Filed: Oct. 4, 2001

(65) Prior Publication Data

US 2002/0077705 A1 Jun. 20, 2002

Related U.S. Application Data

(60) Provisional application No. 60/238,301, filed on Oct. 4, 2000.

(51) Int. Cl.[7] ................................................. A61F 2/80
(52) U.S. Cl. ............................................................ 623/36
(58) Field of Search ......................... 623/27, 32, 33, 623/38, 53, 54, 57, 36; 602/63

(56) References Cited

U.S. PATENT DOCUMENTS

| | | | |
|---|---|---|---|
| 694,325 A | * 2/1902 | Peer | 623/28 |
| 4,463,459 A | 8/1984 | Shorter et al. | 3/30 |
| 4,578,083 A | 3/1986 | Williams | 623/42 |
| 5,211,667 A | * 5/1993 | Danforth | 623/35 |
| 5,800,565 A | 9/1998 | Biedermann | 623/38 |
| 5,888,232 A | 3/1999 | Taylor | 623/38 |

OTHER PUBLICATIONS

Advertisement for Icelock™ attachment system, OSSUR Product Catalogue 2000–2001, Jun. 2000, pp. E3–E4.

* cited by examiner

Primary Examiner—Corrine McDermott
Assistant Examiner—William H Matthews
(74) Attorney, Agent, or Firm—Pedersen & Co., PLLC; Ken J. Pedersen; Barbara S. Pedersen

(57) ABSTRACT

A latch mechanism secures a residual limb to an artificial limb in a comfortable and substantially non-rotational manner. The latch mechanism offers relatively-proximal anchoring of a residual limb in a hard socket, rather than the conventional distal attachment, resulting in ease of donning and doffing of the socket by an amputee. The proximal attachment feature requires no clearance in the bottom of the socket "well" as no part of the latch mechanism is located between the distal end of the residual limb and the bottom inside of the well. The latch mechanism is disposed entirely along the side of the limb and the side of the socket, and extends from the liner on the limb a short distance inside the socket before exiting to the outside of the socket for locking onto the socket side surface. Even though the latch mechanism extends through an aperture in the wall of the socket, a tight gel suction wrap or other seal around the aperture still allows for a reliable suction fit.

15 Claims, 8 Drawing Sheets

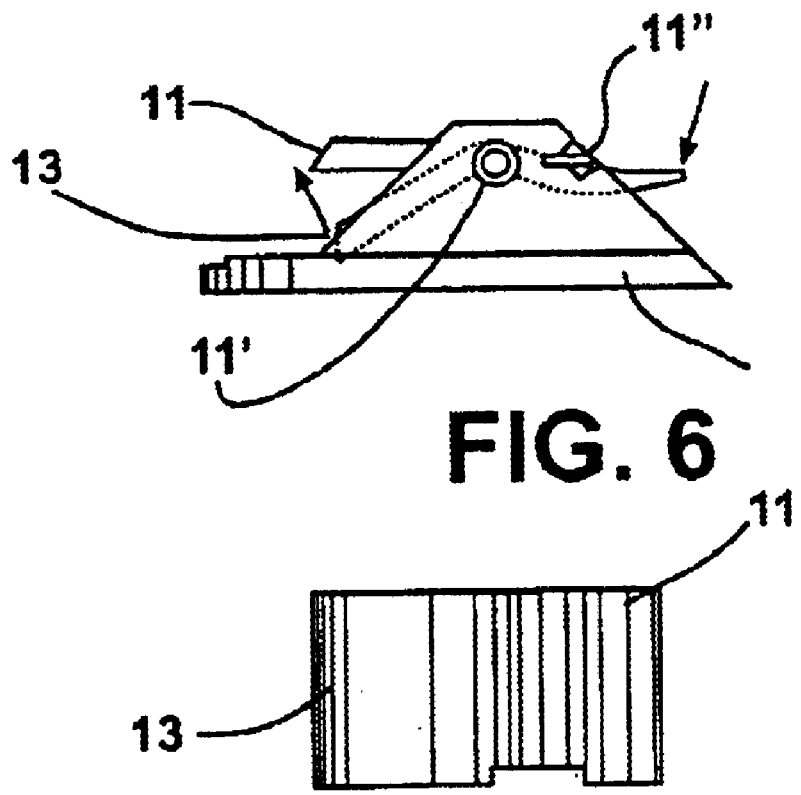

ATTACHMENT SYSTEM FOR PROSTHESIS

This application claims priority from U.S. Provisional Patent Application Serial No. 60/238,301, filed on Oct. 4, 2000, entitled "Attachment System for Prosthesis," the disclosure of which is incorporated herein by this reference.

BACKGROUND OF THE INVENTION

1. Field of the Invention

The present invention relates generally to prosthetics, and, more specifically to an attachment system used in the donning/doffing of a socket onto a residual limb. The present invention more particularly relates to an attachment system that requires little or no clearance inside the socket between the socket and the residual limb, that controls rotation of the prosthesis, and that may be used with a suction-fit socket system. The invented attachment system extends from the side of a liner on the user's limb, through an aperture in the socket, to the outer side of the socket, substantially proximal on the limb and on the socket relative to conventional more "distal" attachment devices. Therefore, the invented attachment may properly be called an exterior, proximal attachment device for a prosthesis.

2. Related Art

For years, many different methods have been used to retain or "suspend" a prosthetic limb on an amputee's residual limb. Gravitational and other forces, for example, from movement of the limbs, tend to cause separation between the prosthetic limb and the patient's residual limb during use. This happens, for example, during the swing phase of gait, when a prosthetic leg is additionally subjected to centrifugal forces. Patients have routinely worn a variety of belts, straps, cuffs, and harnesses to retain their prosthetic limbs against separation from the limb during these periods. But such devices are often inconvenient and may tend to cause chafing against the patient's body, giving rise to sores and abrasions.

The manner in which an artificial limb is suspended and/or attached to the residual limb determines the amount of control an amputee has over the prosthesis. Therefore, by improving suspension/attachment without adding weight and excessive mechanism, the amputee may obtain improved comfort, convenience, and suspension mobility.

A common approach to tackling this problem has led to the design of a roll-on suction liner, which is rolled on the residual limb on its proximal end, and attached at its distal end to a socket or artificial limb. The liner, which is usually fabricated from silicone, or some other gel form, fits snugly over the residual limb and is, in turn, enveloped, especially at its distal end, by the socket of the prosthesis, which is also called a "hard socket." This suspension method is very advantageous for the amputee. It gives the amputee the ability to better control the prosthesis and provides for useful sensory or proprioceptive feedback. Suction suspension also makes a prosthesis feel lighter, compared to other forms of suspension. Unfortunately, only a small percentage of amputees can successfully and comfortably wear a liner without another form of suspension. Typically, therefore, the socket liner is equipped with a detachable attachment component, usually at its distal end, which mates with a locking device, typically in the distal inside region of the socket, and which thereby secures the residual limb to an artificial limb. Hence, the name "distal" attachment or lock is used for this typical design. The locking device in the distal end of the socket generally employs a spring-loaded clutch mechanism or a pin-lock mechanism inside the socket, which locks onto the liner attachment component. The attachment component on the liner is typically a cylindrical barb-shaped structure or frictionally-retained pin.

One problem associated with such designs is the tugging or pull on the distal end of the limb. Most of these locks are not air tight, thus allowing air to flow into the hard socket and to eliminate the "suction." When this happens, the only suspension is the pin, which is a traction suspension, rather than suction. In cases where prosthetic socks are worn outside the liner, there is also a risk of the user's limb being trapped in the socket if the sock is forced into the lock mechanism and then gets stuck. In these incidents, most patients are forced to make emergency trips to their practitioner to be able to get the prosthetic off. Also, the locking device and attachment component cooperate in such a way to permit the barb or pin to lock in a plurality of longitudinal positions, which affects the overall length of the prosthesis. This can make it difficult for the patient to consistently achieve the same prosthetic configuration when the residual limb and the artificial limb are articulated. It should be further noted that, by weight of the lock being added at the distal end of the residual limb or near the distal end of the socket, this can make the prosthetic device feel heavier because of a "lever arm" effect, than if the same weight were placed more proximally. Additionally, many amputees, whether because of the length of their residual limb or their height, do not have room in the suction liner-socket-prosthesis combination for a distal locking mechanism. Or, additionally, use of a distal lock may limit what other prosthetic components that patient may use.

Also, despite the large number of suspension options available, none of the above-mentioned devices act to eliminate rotation between the hard socket and the suction liner. In an attempt to alleviate the rotation problem, a design called a "quad socket" has been used for many years. The quad socket is shaped in a square manner more than a cylindrical manner, and forcing the "cylindrical" limb to fit tightly in this square receptacle makes the prosthesis less apt to rotate on the limb, much as if you made a wheel square. Unfortunately, this is not a very comfortable position for the limb. Today, therefore, there has been a trend toward more naturally-shaped sockets, making rotation control even more difficult.

Therefore, there is still a need for an improved attachment system for prosthetics. Also, there is a need for improving retention of the stump in the socket without sacrificing the patient's comfort and without comprising on expense, weight and simplicity of use of the prosthesis. There also is a need for improving rotation control, which will improve the patient's overall comfort and agility.

SUMMARY OF THE INVENTION

The present invention is an attachment system or "latch mechanism" for connecting a prosthesis to a residual limb of the user. Preferably, the attachment system extends from the side surface of a liner on a residual limb to the outside side surface of a hard socket fitted around the liner and limb. Preferably, the attachment system includes a tab system that connects to the outer side surface of the liner, which tab system extends into the socket along-side the limb and the socket, and through an aperture in the sidewall of the socket. Preferably, the tab system further extends to a lock connected to the outer side surface of the socket, typically about midway or more, proximally, on the outside surface of the socket. Thus, the attachment system is located proximally (nearer the user's torso rather than farther out from the torso)

and externally relative to conventional distal components that are typically inside the socket and at the very end (distally) of the limb, respectively. Mounting the lock proximally rather than conventionally in the "bottom" of the inside "well" of the socket, eliminates the need for extra room inside the socket for the lock component. This also prevents the pulling or tugging on the distal end of the limb that can cause discomfort. The lock is also mounted externally, allowing it to be easily reached by the user, easily maintained, and/or easily retrofit as an add-on feature to existing hard sockets. Also, the externally-mounted lock eliminating jams caused by socks that are often worn over the roll-on liners. Any opening through the socket that is used in the mounting and connecting of the tab to the lock can then preferably be easily resealed by a gel suction wrap/cover, or other air-tight wrap or plug that preferably encases the lock mechanism and aperture, thus allowing and maintaining a "suction" fit between the socket and the liner that improves the function of the prosthetic as discussed above. In this way, a combination of the invented strap and lock system and a suction fit provide superior retention of the artificial limb on the user.

The preferred tab system includes a disk member or "umbrella" that may be adhesively held on the surface of the liner, and an elongated strap or "tab" that extends down distally from the umbrella and longitudinally a short distance along the side surface of the limb. The tab may be secured to the umbrella in such a way that its exact angle relative to the limb's longitudinal axis may be adjusted as desired and then locked in place, for example, by tightening of a bolt. This allows for swinging the tab slightly to a different angle to properly reach and latch into the latch mechanism, so that perfect pre-placement of the umbrella and lock are not absolutely required, but rather, some adjustability for custom fitting is provided. The lock is preferably a buckle-style device, with a spring-biased member with, for example, one or more sharp edges, that frictionally engage transverse detents located between transverse raised ridges on the tab surface. Thus, the tab is inserted into the buckle to the extent desired by the user, and, in a ratchet-like action, the sharp edges wedge into the transverse detents and secure the tab from being pulled out or away from the latch mechanism. Thus, the tab is anchored in the latch mechanism, and the socket is held closely on the residual limb until the user chooses to unbuckle the latch mechanism. Therefore, the latch mechanism is easily accessible, effective, simple, and easy to use. The versatility and simplicity, and non-interfering design of the invented latch mechanism help provide reliable and comfortable suspension for an artificial limb on a great number of persons with limb deficiency.

BRIEF DESCRIPTION OF THE DRAWINGS

FIGS. 6 and 8, respectively, are side and top views, respectively, of one embodiment of the buckle-style lock ("buckle") of the present invention.

FIGS. 7 and 10, respectively, are top and side views of the lever of the buckle embodiment of FIGS. 6 and 8.

DETAILED DESCRIPTION OF THE INVENTION

Figure 1:
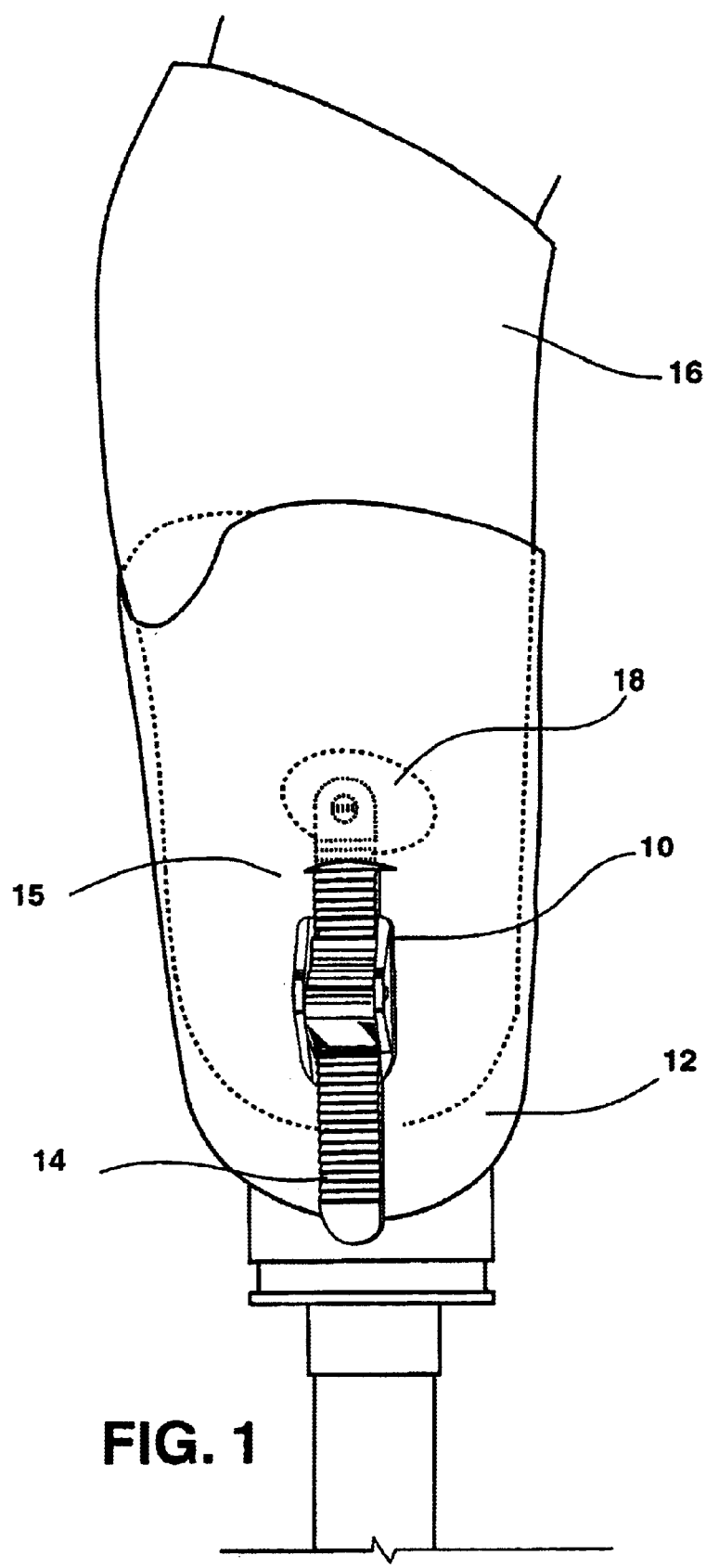
FIG. 1 is a side view of one embodiment of the prosthetic latch system (attachment system) according to the invention, installed on a user's residual limb.
Figure 2:
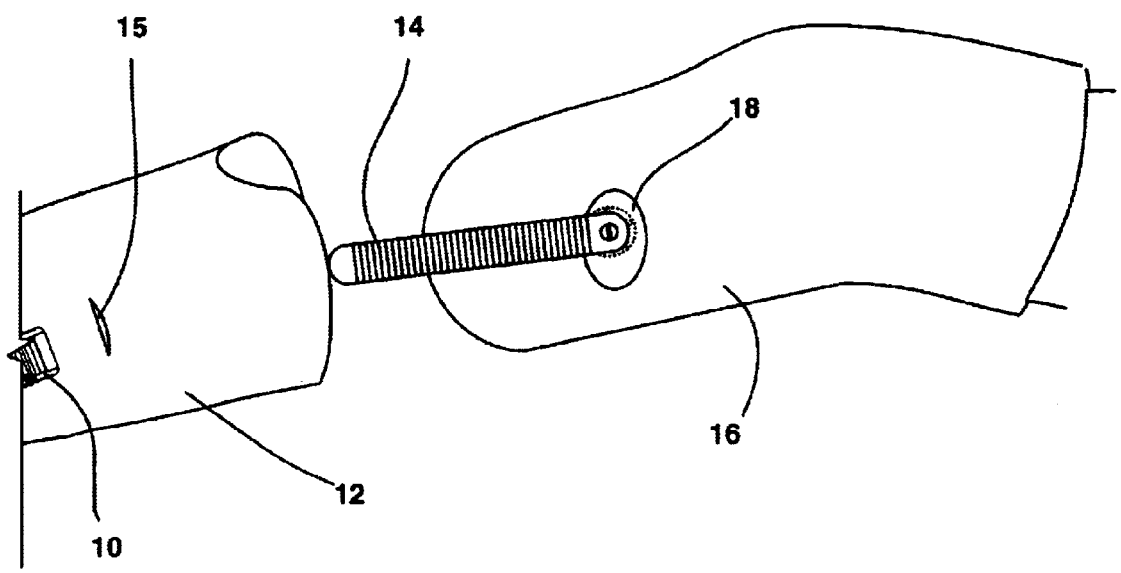
FIGS. 2–5 are sequential, side views of the preferred prosthetic latch system of the present invention, and a depiction of the 4-step process of the latch system being used to install a prosthetic on a limb of an amputee.
Figure 3:
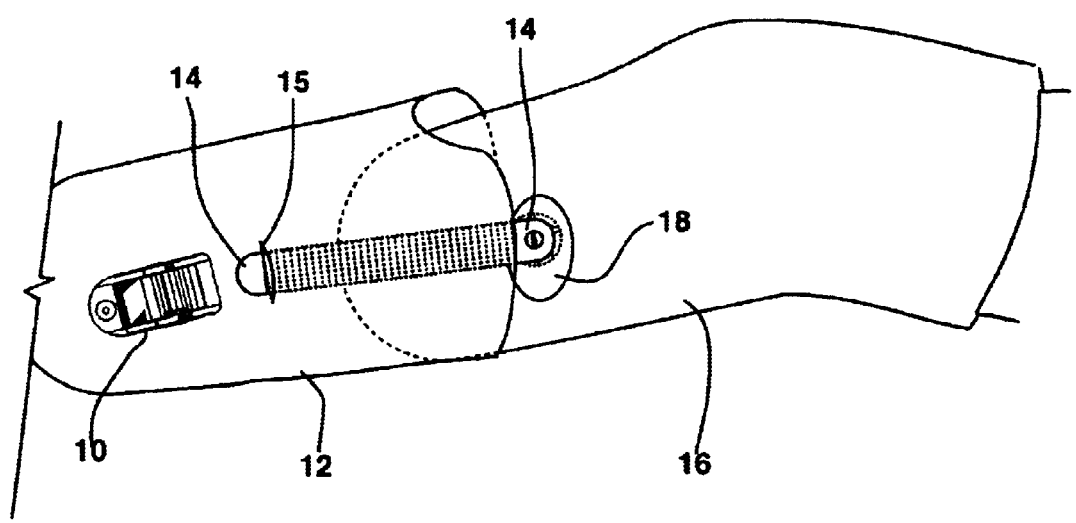
Figure 4:
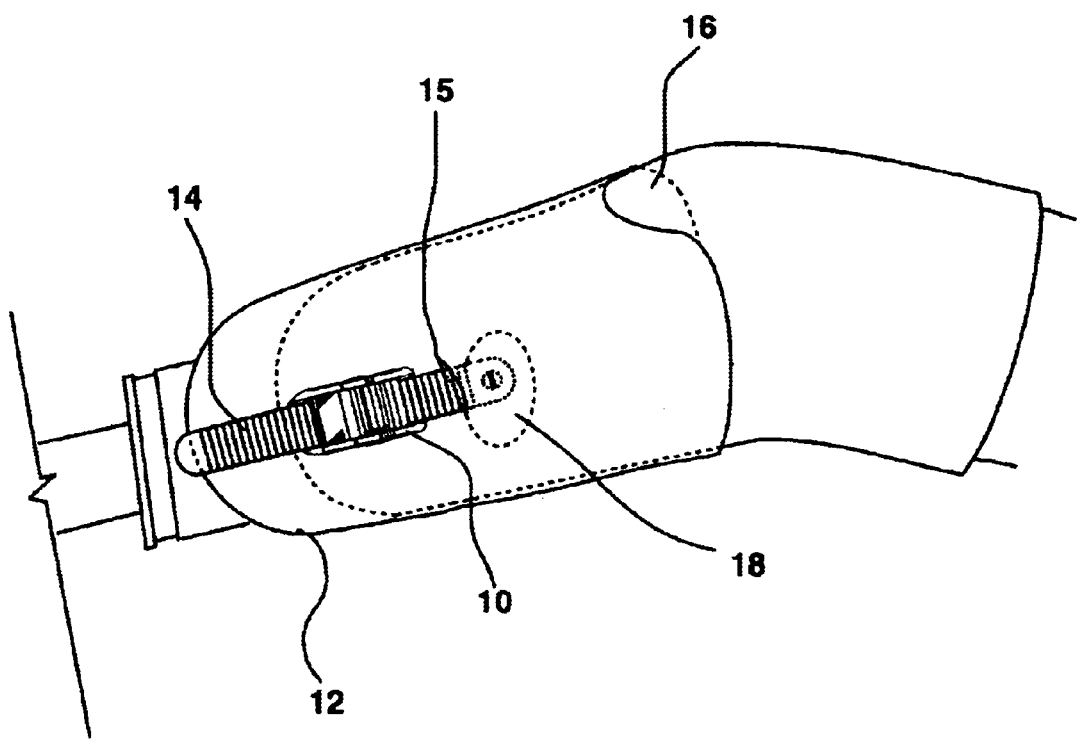
Figure 5:
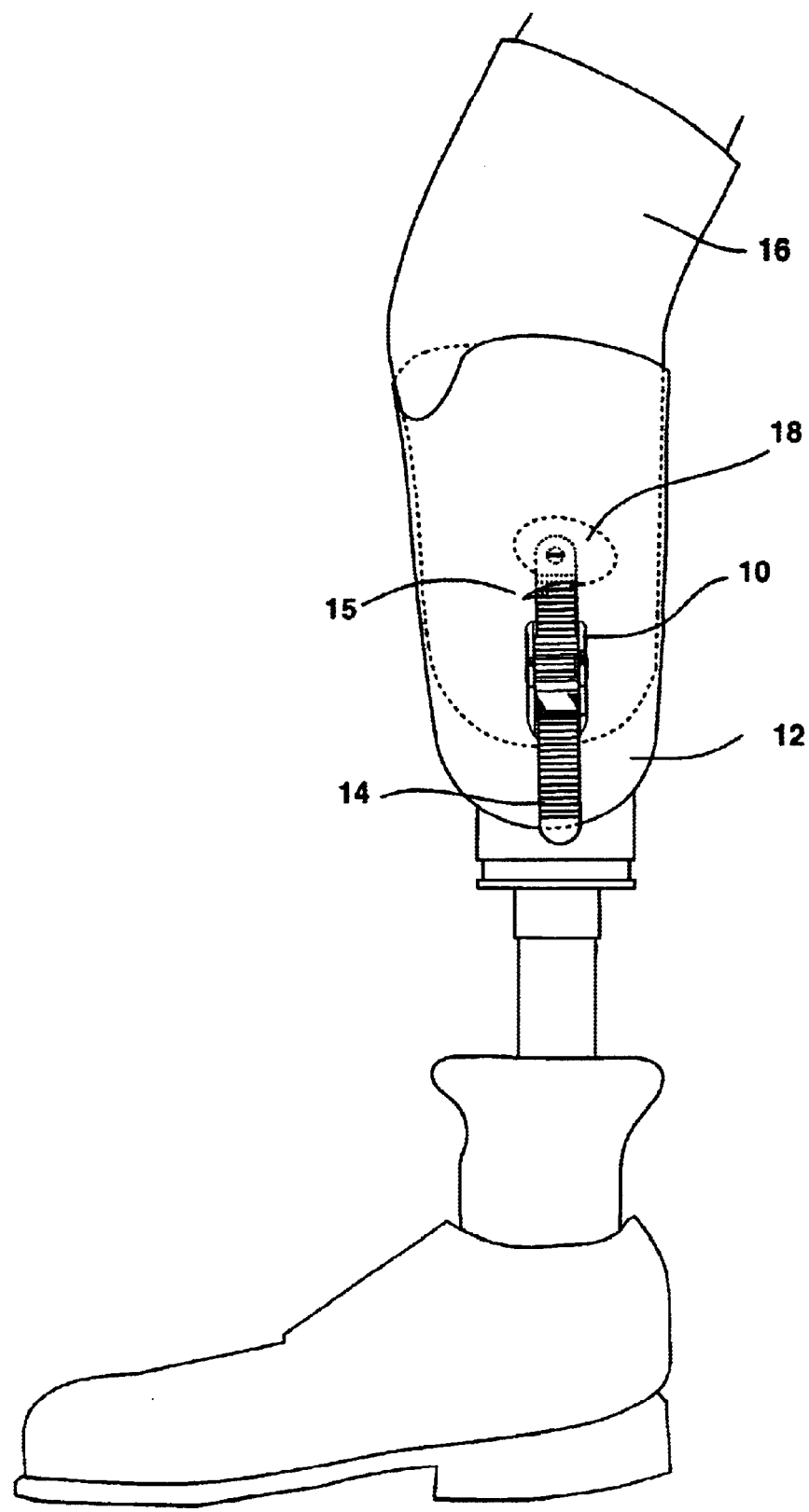
Figure 9:
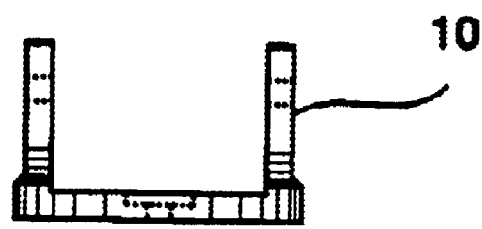
FIG. 9 is a front view of the base frame of the buckle of FIGS. 6–8, and 9.
Figure 10:
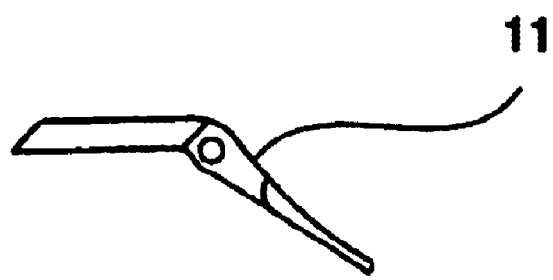
Figure 11:
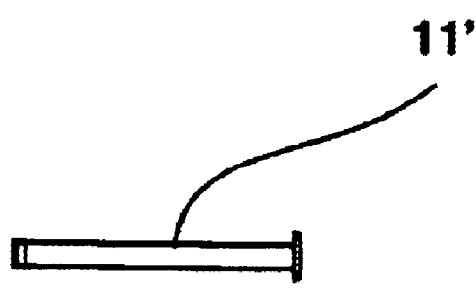
FIG. 11 is a front view of the pin of the buckle of FIGS. 6–10.
Figure 12A:
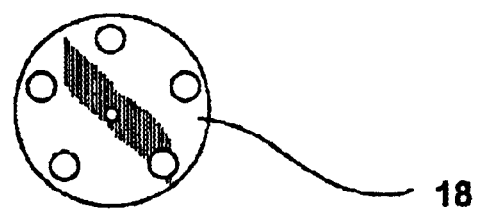
FIG. 12A is a plan view of one embodiment of an umbrella plate for attachment to an outside surface of a liner.
Figure 12B:
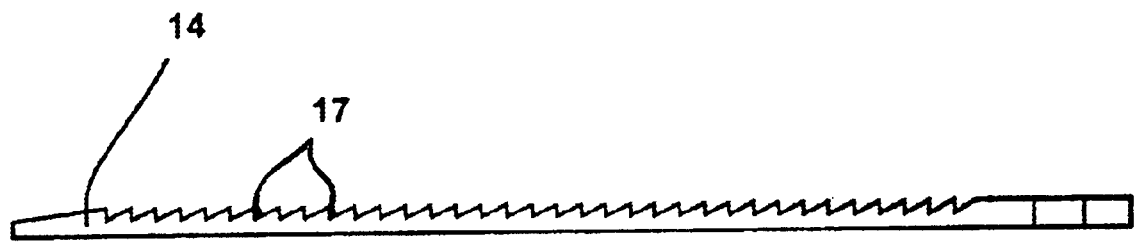
FIG. 12B is a side view of one embodiment of a tab strap according to the invention, for cooperating with, and connecting, the buckle-style lock and the umbrella plate.

Referring to the Figures, there is shown one preferred embodiment, but not all embodiments, of the present invention, which is referred to herein as a "latch system" or "attachment system." The preferred buckle-style lock of the invented latch system includes base 10, which is mounted externally (on the outside surface of the hard socket 12) and proximally (closer to the amputated limb) than conventional "distal" locks that are mounted near the distal end of the socket, typically at the bottom of the inside "well" of the hard socket 12. Connected to base 10 are a lever 11 and pin 11' with e-clips 11", which together create a biased system for receiving and capturing tab 14, which is preferably an elongated strap. Tab 14, as discussed below, is preferably secured to the liner 16, by means of a umbrella 18, and is long enough to comfortably and conveniently extend from the middle to upper side of the liner (see FIGS. 6–11). Base 10 may be screwed or glued to socket 12, or even molded integrally with socket 12, to anchor the buckle-style lock onto the socket preferably part way up the side of the socket.

Tab 14 is connected at its proximal end with a screw to liner 16, which liner may be attached by glue in a conventional manner to umbrella 18. Umbrella 18 is generally a plate-like structure, with preferably a slightly-concave inner surface for contacting the glue, and with apertures at various locations on the umbrella to assist in the glue adhesively connecting the umbrella 18 to the liner 16 outside side surface. However, umbrella 18 may also be sewn onto or into liner 16, or it may be formed integrally with liner 16. Also, alternatively, other shapes of an attachment plate or other attachment means may be used instead of the umbrella, as long as preferably they are thin and easily slide/fit into the socket without causing discomfort and without requiring significant clearance inside the socket.

When hard socket 12 is installed on the residual limb, it extends up over and around liner 16 and umbrella 18. Tab 14 extends from umbrella 18 on liner 16 a short distance on the inside of socket 12 through an aperture 15 in socket 12 out to the outside of socket 12. There, the tab 14 continues to extend to and through the preferred buckle-style lock attached on the outside surface of the socket 12. The buckle-style lock adjustably receives the distal end of the tab 14, by means of the tab extending through the lock between the base 10 and the lever 11. The tab 14 is pushed/pulled through the buckle-style lock up to the point where the hard socket 12 is securely but comfortably secured around and connected to liner 16 via the tab and umbrella combination. This way, the advantages of the invention are realized.

Therefore, the invented prosthetic latch system includes a method of attaching a prosthetic socket to a liner on an amputated lower or upper extremity. It preferably comprises three components, the tab secured to the liner and extending through an aperture in the socket to become attached to a lock on the outside surface of the socket. The aluminum attachment plate or umbrella 18, which is about ¾" in diameter and ¼" thick, is connected to a custom or pre-manufactured roll-on liner 16 (i.e., ICEROSS, ALPHA, LUXURY LINER, ALPS, SILIPOS (all trademarks)) more towards the proximal end of the liner (not at its distal end) with adhesive, for example. Modern urethane liners are especially preferred. The umbrella 18 may have holes drilled all around the attachment area receive and to better grip with the adhesive. The tab 14 is then attached to the umbrella 18 with, for example, a 10/24-spanner bolt or screw. The screw is then tightened down to the umbrella 18, rather than allowing the tab 14 to pivot around the screw, which results in the tab 14 being more adjustable, allowing it to lock even if the tab 14 or lock mechanism have been attached to their respective structures in less-than-perfect position or location.

The release button of the lock mechanism of the invention is buckle lever 11, which features sharp edge 13. The top surface of base 10 ramps up in thickness in the distal direction. This provides for easier tab 14 entry into the latch mechanism, and increasing pressure on the tab when engaged by means of the buckle level 11 pressing/ratcheting against the tab. Edge 13 engages sharp transverse detents 17 on tab 14 passing through the lock mechanism. Any pull on tab 14 is resisted by the engagement of edge 13 in detents 17 and the pressure of lever 11 against e-clips 11". The base 10 of the lock mechanism is then mounted externally, and proximally, to the hard socket 12 using, for example, a rivet or adhesive. The lock mechanism is attached in whatever position the prosthetist deems most advantageous and convenient for the patient. The lock mechanism is attached to the exterior of the socket at a location determined by test socket fitting, but in any event, not at the distal end of the socket. An access hole 15 is created in the socket just proximally the lock mechanism. This access hole 15 is where the tab 14 will come through the hard socket 12 to connect with the base 10 and release lever (or "button") 11.

After mounting of the base 10 of the lock mechanism onto the socket, the umbrella 18 onto the liner, and tab 14 onto the umbrella are complete, the roll-on prosthetic liner 16 of choice is applied to the patient. The patient can then step into the hard socket 12 and engage the latch mechanism, by inserting the tab through the aperture and into the lock mechanism. This procedure may also be used in the retrofitting of the latch mechanism to an existing prosthetic.

If a new prosthetic is being created, the liner 16 is applied to the patient, and the ideal location for the umbrella 18 is marked on liner 16. A mold over the patient's limb and liner 16 is then taken. After the mold and liner 16 are removed, the umbrella 18 is then attached to the liner 16 in the location marked. From the mold the hard socket 12 is created, and the base 10 of the lock mechanism is attached in the proper location on the outside of hard socket 12, and then the access hole 15 is created in hard socket 12 as above.

EXAMPLES

The invented latch system was fit to three test patients. All three of these patients utilized ALPHA™ liners in a normal manner. The locking tab was attached to the ALPHA™ liners in a normal manner. Two of these patients were unilateral transtibial amputees, and one patient was a unilateral congenital above-knee amputee. The above-knee amputee was a congenital amputation resulting from PFFD, and his amputation level was consistent with a knee disarticulation level. All three of these patients either demonstrated problems with conventional distal pin-lock systems, or, in the case of the transfemoral amputee, did not have sufficient room to install any of the distal locking mechanisms currently on the market. These patients have been using the prosthetic lock suspension according to the present invention on their prosthesis on a daily basis. These patients were all experimentally fit in June of 2000 and no problems have been encountered with mechanical failures or with patient acceptance or satisfaction. We continue to monitor these patients at 2–3 week intervals.

One may see, after reviewing the disclosure of this Description and the Drawings, that the invented latch mechanism may provide a comfortable and easy-to-use system for attaching a prosthesis, wherein the system tends to prevent rotation of the prosthesis on its longitudinal axis (axis extending between its proximal end and distal end) relative to the amputated limb. By providing one of the invented side-located, "proximally-located" latch mechanisms, such rotation is limited or prevented. This is because a tab or strap extends from a fixed anchor location on the side of the liner/limb to a fixed anchor location on the side of the socket, thus connecting those two fixed locations together at substantially a fixed distance apart, thereby not allowing the anchor location on the socket to rotate any significant distance away from the anchor location on the liner. Although one of the invented latch mechanism systems is preferred, more than one may possibly be used, for example, at two positions around the side of the limb/socket.

Although this invention has been described above with reference to particular means, materials and embodiments, it is to be understood that the invention is not limited to these disclosed particulars, but extends instead to all equivalents within the broad scope of this disclosure and the following claims.

What we claim is:

1. An attachment system for a prosthesis, comprising:
   a suction liner adapted to fit snugly over a residual limb of a user to be secured to the residual limb, said suction liner having a proximal end and a distal end, and an outside surface;
   a strap secured to said suction liner's outside surface at a location more proximal than the distal end of the suction liner, said strap extending towards the distal end of said suction liner;
   a socket of a prosthesis fitting over said suction liner and said residual limb, said socket having a proximal end and a distal end, an inside surface, and an outside surface;
   an aperture in said socket allowing said strap to pass from the inside surface of the socket to the outside surface of the socket, said aperture being placed at a location more proximal than the distal end of said socket; and
   a lock mechanism on the outside surface of said socket receiving and securing said strap;
   wherein the prosthesis is adapted to secure to the residual limb by the suction liner being secured to the residual limb and the strap extending between the suction liner and the socket.

2. The attachment system of claim 1, wherein the socket further connects to said suction liner with an airtight suction fit so that the socket is suction-suspended from the suction liner, and wherein said aperture in said socket is sealed after the strap passes through the aperture, to prevent air from entering from the outside of the socket in between the socket and the suction liner and maintain suction-suspension of the socket from the liner.

3. The attachment system of claim 1, wherein the suction liner is a silicone suction liner.

4. The attachment system of claim 1, wherein the suction liner is a urethane suction liner.

5. An attachment system for a prosthesis, comprising:
a liner for fitting over the residual limb of a user, said liner having a proximal end and a distal end, and an outside surface;
a strap secured to said liner's outside surface at a location more proximal than the distal end of the liner, said strap extending towards the distal end of said liner and wherein said strap has a plurality of transverse detents on the top surface thereof;
a socket for fitting over said liner and said residual limb, said socket having a proximal end and a distal end, an inside surface, and an outside surface;
an aperture in said socket for allowing said strap to pass from the inside surface of the socket to the outside surface of the socket, said aperture being placed at a location more proximal than the distal end of said socket; and
a lock mechanism on the outside surface of said socket for receiving and securing said strap.

6. The attachment system of claim 5 wherein said lock mechanism comprises a buckle device with a spring-biased lever with a sharp edge for engaging one of said transverse detents.

7. An attachment system for a prosthesis comprising:
a roll-on suction liner adapted to snugly fit over the residual limb of a user to be secured to the residual limb, said roll-on suction liner having a proximal end and a distal end, and an outer side surface between the proximal end and the distal end;
a strap secured to said roll-on suction liner's outer side surface at a location between the distal end and the proximal end, said strap extending towards the distal end of said roll-on suction liner;
a socket fitting over said roll-on suction liner and forming a suction-fit with the roll-on suction liner, said socket having a proximal end and a distal end, an inside surface defining a well for receiving the roll-on suction liner and the residual limb, and an outside surface;
an aperture in said socket from the inside surface to said outside surface, said aperture being placed at a location between the distal end of the socket and the proximal end of the socket;
a lock mechanism on the outside surface of said socket;
wherein said strap extends from the roll-on suction liner's outer side surface through the aperture and to said lock mechanism, and wherein said lock mechanism grips the strap to hold the socket in fixed relation to the roll-on suction liner; and
wherein said aperture is sealed so that air does not leak into the well to break the suction-fit between the socket and the roll-on suction liner.

8. An attachment system for a prosthesis, comprising:
a liner for fitting over the residual limb of a user, said liner having a proximal end and a distal end, and an outer side surface between the proximal end and the distal end;
a strap secured to said liner's outer side surface at a location between the distal end and the proximal end, said strap extending towards the distal end of said liner, wherein said strap has a plurality of transverse detents on its top surface;
a socket for fitting over said liner and said residual limb, said socket having a proximal end and a distal end, an inside surface defining a well for receiving the residual limb, and an outside surface;
an aperture in said socket from the inside surface to said outside surface, said aperture being placed at a location between the distal end of the socket and the proximal end of the socket;
a lock mechanism on the outside surface of said socket;
wherein said strap extends from the liner's outer side surface through the aperture and to said lock mechanism, and wherein said lock mechanism grips the strap to hold the socket in fixed relation to the liner.

9. The attachment system of claim 8 wherein said lock mechanism comprises a buckle device with a spring-biased pivoting lever with an edge for engaging one of said transverse detents to releasably lock the strap in the lock mechanism.

10. The attachment system of claim 8, wherein the socket has a longitudinal axis between the proximal end and the distal end of the socket, and wherein the strap is pulled tight in, and retained tight in, the lock mechanism, so that the socket does not move longitudinally away from the liner, and so that the socket does not rotate on the longitudinal axis.

11. An attachment system for a prosthesis consisting of:
a liner adapted to fit over a residual limb of a user to be secured to the residual limb, said liner having an outer side surface for lying on a side of the residual limb;
a strap secured to said liner's outer side surface;
a prosthesis socket for fitting over said liner and said residual limb, said socket having a side wall for extending generally parallel to the outer side surface of the liner and the side of the residual limb, the side wall having an inside surface and an outside surface;
an aperture through said socket side wall from the inside surface to said outside surface;
a lock mechanism on the outside surface of said socket side wall;
wherein said strap extends from the liner's outer side surface through the aperture and to said lock mechanism, and wherein said lock mechanism grips the strap to hold the socket in fixed relation to the liner;
wherein the prosthesis is secured to the residual limb by the liner being secured to the residual limb and the strap extending between the liner and the socket.

12. An attachment system for a prosthesis, comprising:
a liner for fitting over the residual limb of a user, said liner having an outer side surface for lying on a side of the residual limb;
a strap secured to said liner's outer side surface, wherein said strap has a plurality of transverse detents on its top surface;
a socket for fitting over said liner and said residual limb, said socket having a side wall for extending generally parallel to the outer side surface of the liner and the side of the residual limb, the side wall having an inside surface and an outside surface;
an aperture through said socket side wall from the inside surface to said outside surface;
a lock mechanism on the outside surface of said socket side wall;
wherein said strap extends from the liner's outer side surface through the aperture and to said lock mechanism, and wherein said lock mechanism grips the strap to hold the socket in fixed relation to the liner.

13. The attachment system of claim 12 wherein said lock mechanism comprises a buckle device with a spring-biased pivoting lever with an edge for engaging one of said transverse detents to releasably lock the strap in the lock mechanism.

14. The attachment system of claim 12, wherein the socket has a longitudinal axis parallel to the socket side wall and extending between a proximal end of the socket and a distal end of the socket, and wherein the strap is pulled tight and retained tight in the lock mechanism, so that the socket does not move longitudinally away from the liner, and so that the socket does not rotate on its longitudinal axis.

15. An attachment system for a prosthesis comprising:
a prosthesis having a hard socket with a side wall surrounding and defining an interior well for receiving a user's residual limb;
a roll-on socket liner adapted to attach to a user's residual limb by snugly surrounding the residual limb, the roll-on socket liner being received in the socket;
a strap connecting said roll-on socket liner to said hard socket by passing from the well through the hard socket side wall at a location proximal to a distal end of the hard socket and connecting to an outer side surface of the hard socket.

\* \* \* \* \*